United States Patent [19]

Nielsen

[11] Patent Number: 5,772,958
[45] Date of Patent: Jun. 30, 1998

[54] METHOD AND APPARATUS FOR THE PASTEURIZATION OF A CONTINUOUS LINE OF PRODUCTS

[75] Inventor: Jørgen Tage Nielsen, Copenhagen N, Denmark

[73] Assignee: Sander Hansen A/S, Glostrup, Denmark

[21] Appl. No.: 693,295

[22] PCT Filed: Feb. 9, 1995

[86] PCT No.: PCT/DK95/00062

§ 371 Date: Aug. 16, 1996

§ 102(e) Date: Aug. 16, 1996

[87] PCT Pub. No.: WO95/22352

PCT Pub. Date: Aug. 24, 1995

[30] Foreign Application Priority Data

Feb. 18, 1994 [DK] Denmark ................................. 0204/94

[51] Int. Cl.⁶ ............................. A61L 2/18; A61L 2/20; A23C 3/027; B08B 3/04
[52] U.S. Cl. .................................. 422/1; 422/26; 422/38; 422/292; 422/300; 422/307; 422/308; 426/407; 426/401; 426/521; 426/522; 99/483; 134/72; 134/131
[58] Field of Search .......................... 134/131, 72; 422/1, 422/38, 292, 300, 307, 308, 26; 426/407, 409, 401, 521, 522; 99/483

[56] References Cited

U.S. PATENT DOCUMENTS

| | | | |
|---|---|---|---|
| 2,282,187 | 5/1942 | Herold et al. | 426/407 |
| 2,652,841 | 9/1953 | Kurt | 136/46 |
| 4,023,618 | 5/1977 | Kun et al. | 165/175 |
| 4,441,406 | 4/1984 | Becker et al. | 99/275 |
| 4,490,401 | 12/1984 | Becker et al. | 426/407 |
| 5,310,566 | 5/1994 | Baudendistel | 426/231 |

FOREIGN PATENT DOCUMENTS

| | | |
|---|---|---|
| 430 907 A2 | 5/1991 | European Pat. Off. . |
| 90/02707 | 3/1990 | WIPO . |
| 91/15128 | 10/1991 | WIPO . |

*Primary Examiner*—Robert J. Warden
*Assistant Examiner*—Alex Noguerola
*Attorney, Agent, or Firm*—Pennie & Edmonds LLP

[57] ABSTRACT

The method and the apparatus according to the invention relate to pasteurization of products in a tunnel pasteurizer. In the application of heating systems comprising water/steam heat exchangers in the zones for heating of sprinkling water, the pipelines and the valves for controlling the water and the steam become very complex and vulnerable, and the number of analog valves for steam become equal to the number of heat exchangers as a minimum. Leakages in analog valves for steam are frequent after some time in operation. According to the invention this problem is eliminated in that hot water is taken out under low pressure from a heating source (7) comprising a heat-insulted storage tank and a shared source of heat, where the water is circulating constantly, said hot water being supplied in a controlled amount directly to each zone (14b, . . . , 14n), in which the products are to be heated, and the hot water in the unit being maintained at a temperature, which is substantially higher than the temperature of the sprinkling water in the zone having the highest temperature. A reduced consumption of peak energy after a failure of equipment has terminated as well as a faster reestablishment of the operational temperature are hereby achieved as compared to the methods known up to now.

8 Claims, 1 Drawing Sheet

METHOD AND APPARATUS FOR THE PASTEURIZATION OF A CONTINUOUS LINE OF PRODUCTS

This application is a 35 U.S.C. 371 of PCT/DK95/00062 which is now WO95/22352.

BACKGROUND OF THE INVENTION

The invention relates to a method for the pasteurization of a continuous line of products in an apparatus having a heating area, a pasteurization area and a cooling area as well as means of conveyance for carrying the products through the areas in the order indicated in a regular motion from the inlet of the apparatus to the outlet hereof, whereby heating, pasteurization and cooling are effected by heat transfer between the products and a fluid, preferably water, which is sprinkled over the products, the areas being divided into zones extending in the direction of motion of the products, and the temperature of the water in the individual zone being adapted to the desired sequence of the heat transfer for the zone.

The invention also relates to an apparatus for use in the implementation of the said method, said apparatus having a a heating area, a pasteurization area and a cooling area as well as means of conveyance for carrying the products through the areas in the order indicated in a regular motion from the inlet of the apparatus to the outlet hereof, whereby heating, pasteurization and cooling are effected by heat transfer between the products and a fluid, preferably water, which is sprinkled over the products, the areas being divided into zones extending in the direction of motion of the products, and the temperature of the water in the individual zone being adapted to the desired sequence of the heat transfer for the zone.

In the production of products which are perishable by bacterial flora it is well-known art to destroy the bacterial flora by pasteurization, which in the case of a continuous line of products is accomplished in a so-called tunnel pasteurizer.

A continuous line of products, which must necessarily be pasteurized in order to achieve keeping qualities, is known for example from the brewery industry in the form of beer or similar products, which are contained in bottles.

Tunnel pasteurizers are known for example from DK Patent Specification No. 161.618, U.S. Pat. No. 4.490.401 and No. 4.441.406, GB Printed Specification No. 2.182.542 and EP Patent Specification No. 0.437.499.

In the known tunnel pasteurizers the products are pasteurized in a regular progressing movement from an inlet to an outlet. During this movement the products are heated gradually, whereby the pasteurization is accomplished, and normally a gradual cooling down will take place eventually in order to stop the pasteurization process. The apparatuses may therefore be divided into a heating area, a pasteurization area and a cooling area in the said order.

All known tunnel pasteurizers do not necessarily comprise a heating and a cooling area, however, in the brewery industry this is normally the case, since the purpose of gradual heating and gradual cooling is in part to prevent breaking of the containers of the products, which are normally glass bottles, as a result of abrupt changes of temperature, and in part to utilize a heat exchange between the heating and the cooling areas.

The heat transfer to container products is normally accomplished by spraying the containers with a heated fluid, preferably water, as the products are carried forward along the apparatus on a conveyor belt, which the sprinkling water can pass through. In such cases bottom vessels are provided underneath the conveyor belt, and from there the sprinkling water can be pumped up to a higher level to the effect that sprinkling can continue.

The temperature of the sprinkling water in the individual zone is adapted carefully according to the products, the lengths of the zones in the apparatus and the speed of the conveyor belts in order that the products receive the prescribed degree of pasteurization.

In the known pasteurizers the water is heated by means of sources of heat, which may be in the form of bodies heated by electricity and submerged in the water. The water may also be heated simply by feeding steam out into the water.

Normally, heat exchangers are used for heating the water in the zones, the heat exchangers being connected to each individual zone, in which the products are to be heated, and water and steam are supplied through their own separate circulation, the steam in most known apparatuses being supplied from a shared steam supply source with the application of so-called analog valves for the control of the steam admission for the heat exchanger provided in the individual zone.

In the apparatuses which are described in the two above mentioned U.S. Pat. No. 4.490.401 and No. 4.441.406 a central source of heat comprising a hot water storage tank is also provided, in addition to heat exchanges connected to the individual heating zones. The hot water storage tank contains water, which has been heated by sprinkling over warm products, which are to be cooled. The water is then utilized as a buffer storage to be used following a failure of equipment in the tunnel pasteurizer, the water being distributed to the individual zones via analog valves connected to each individual zone.

It will be understood that analog valves refer to valves, which can be adjusted to deliver a certain amount of fluid, in contrast to valves, which are either open or closed (on/off valves).

In the application of heating systems with water/steam heat exchangers in each individual zone, the pipe lines and the valves for controlling the sprinkling liquid and the steam become very complex and vulnerable, and the number of analog valves for steam become equal to the number of heat exchangers as a minimum.

Leakages in analog valves for steam are frequent after they have been in use for some time. In analog valves for steam in a traditional apparatus, in which are provided heat exchangers for each individual zone, leakages correspond to uncontrolled heating of the sprinkling fluid passing the heat exchanger, and the result therefore is an inappropriate consumption of cooling water in order to keep the temperature of the sprinkling water down at the predetermined temperature of the zone during a constant and regular movement of the conveyor belt in normal operation.

In spite of these drawbacks the known apparatuses are normally dependable in service. Nonetheless, any failure of equipment in substantially more complex apparatuses can cause that the conveyor belt of an apparatus must be stopped or its speed at least reduced in order to avoid a pile-up of products.

The consequence is that products which are still in the pasteurization zone become overpasteurized if the temperatures of the sprinkling fluid are maintained.

However, if these temperatures are lowered, there is a risk that the products still being in the zone as the failure of equipment has terminated are underpasteurized, unless heating can take place sufficiently fast. Underpasteurization is worse that overpasteurization, since underpasteurization will considerably reduce the shelf life of the products.

It is therefore an object of the present invention to provide a method of avoiding the drawbacks related to a complex pipe layout and leakages in analog valves for steam as well as of controlling the temperature of the sprinkling water during and after a failure of equipment to the effect that a faster reheating of underpasteurized products after the failure of equipment has terminated as compared to the technique known up to now, and overpasteurization of the products during the failure of equipment is also avoided.

SUMMARY OF THE INVENTION

This object is achieved by means of a method of the kind described in the introduction, which method is advantageous in that hot water is taken out under low pressure from a heat unit comprising a heat insulated storage tank and a shared source of heat, where the water is circulating constantly through the heat unit, said hot water being supplied in a controlled amount directly to each zone, in which the products are to be heated, the hot water in the unit being maintained at a temperature, which is substantially higher than the temperature of the sprinkling water in the zone having the highest temperature.

By means of this method a considerable simplification as well as a higher degree of operational reliability are achieved in an apparatus for use in the implementation of the method, in addition to which it is also achieved that the product can be heated within a very short time following a failure of equipment, without a large peak consumption of steam because of heat energy which is stored in the storage tank, to the effect that underpasteurization is avoided in the zones, in which the temperature of the sprinkling water has become lower that the predetermined reference temperature.

The invention also relates to an apparatus for use in the implementation of the said method and is of the type described in the introduction, which apparatus is advantageous in that the apparatus has a heat unit comprising a heat insulated storage tank and a shared source of heat, which is connected to the storage tank and is adapted to heat the water and to circulate the water constantly in the storage tank, a first pipeline extending from the heat unit and a shared second pipeline for cold water supply, said pipelines being interconnected at each zone to be heated via a three-way valve, the third duct of which via an analog valve being connected to a third pipeline for admission of sprinkling water to the zone, and in that the heat unit is adapted to maintain the water at a temperature, which substantially exceeds the temperature of the sprinkling water in the zone having the highest temperature.

A considerable simplification of the total pipe layout in the apparatus is hereby achieved, to the effect that controlling of the individual valves become less complex, and a higher degree of operational reliability is reached.

With the application of a water/steam heat exchanger as a source of heat in the apparatus according to the invention, the number of analog valves for steam is minimized to comprise a single analog steam valve only, namely the analog steam valve, which carries steam to the shared heat exchanger, as a result of which the frequent leakages, which are known from the large number of analog steam valves of the known apparatuses, are avoided.

A leakage of this single analog steam valve has only a minor effect on the overall effect of the apparatus, and on the overall consumption of cooling water because the water in the storage tank is constantly circulating through the heat exchanger and is still subjected to heating.

The dependent claims relate to preferred procedures respectively preferred embodiments of apparatuses for use in the implementation of the method, the advantages of the contents of the dependent claims being described below.

The method according to the invention will be explained in detail below on the basis of tunnel pasterurizers apparatuses used for example in the brewery industry for pasteurization of products to increase the shelf life hereof, the apparatuses forming part of a bottling unit, for example for the production of beer or similar products in glass bottles, and with reference to the drawing, which illustrates in isometry a tunnel pasteurizer according to the invention.

BRIEF DESCRIPTION OF THE DRAWING

In the drawing is illustrated a part of one end of a tunnel pasteurizer according to the invention, the apparatus being generally referred to with the reference number 1.

DESCRIPTION OF THE PREFERRED EMBODIMENT

Figure 1:
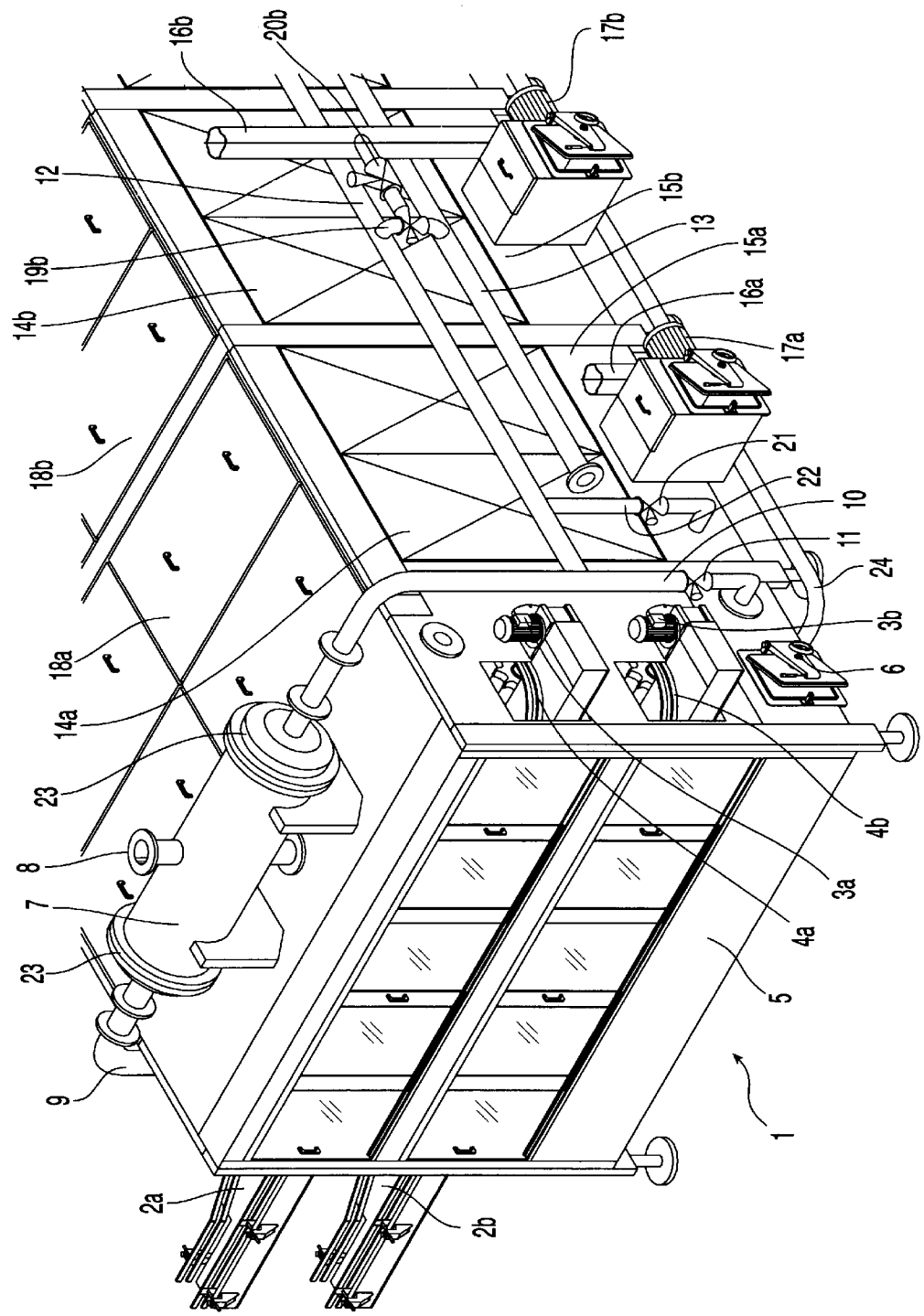

Two conveyor belts 2a, 2b lead to the end of the apparatus, and at the end of each conveyor belt rails 4a, 4b are provided for diversion of bottles, which are on the belts, to the effect that the bottles are carried lengthwise through the apparatus 1. The conveyor belts are driven by motors 3a, 3b.

The apparatus 1 has at the end illustrated a heat unit comprising a heat insulated storage tank 5, which is at the end wall provided with a manhole 6 for admittance to the interior of the storage tank 5 for maintenance purposes.

On the top of the apparatus 1 above the conveyor belts 2a, 2b is provided a heat exchanger 7, which is adapted to heat water by means of steam, which through a pipe 8 is supplied from a steam supply source, which is not illustrated, the steam supply being controlled by an analog valve for steam, which is likewise not illustrated.

The water is carried to the heat exchanger 7 through a first pipe 9 and flows out again through a second pipe 10 after heating, the water being made to circulate under low pressure through the heat exchanger 7 and the storage tank 5 in heated condition by means of a pump, which is not illustrated in the drawing.

The water is heated in the heat exchanger 7 and maintained at a temperature, which substantially exceeds the temperature of the sprinkling water in the zone having the highest temperature, as will be explained below. The water is thus heated advantageously up to between 80° and 90° C.

The heat insulated storage tank 5 is designed to have a large cubic capacity.

The first pipe 9 and the second pipe 10 extend along the side of the apparatus 1 between the storage tank 5 and the heat exchanger 7. In the second pipe 10 is provided a first valve 11 for the purpose of opening and closing off the circulation of the heated water.

A first pipeline 12 is connected between the heat exchanger 7 and the first valve 11, said pipeline extending along the side of the apparatus 1 and along the zones, as will be explained below.

The first valve 11 is a so-called open/closed valve (on/off valve), which is adapted to either let the hot water pass or to prevent its passage. If hot water passes through the on/off valve 11, the pressure in the second pipe 10 will be low, to the effect that only a small amount of water is pressed out into in the first pipeline 12, of course provided that there are no open draw-off cocks along the first pipeline 12.

Conversely, a large amount of hot water will be pressed out into the first pipeline 12 in the opposite condition, if the on/off valve is adjusted to close off passage of hot water in the direction towards the storage tank 5.

A second pipeline 13 carrying cold water extends parallel to the first pipeline 12 along the apparatus 1.

The apparatus is divided into a number of areas comprising as minimum a heating area, a pasteurization area, and a cooling area, and these areas may be divided into a number of zones 14a, 14b, . . . , 14n.

The zones 14a, 14b, . . . , 14n each comprises a bottom vessel 15a, 15b, . . . , 15n, and a pipeline 16a, 16b, . . . , 16n, which can carry water from the bottom vessel 15a, 15b, . . . , 15n to the top of the zone, from which the water can trickle down in a manner, which is not illustrated in detail, and over the products, which are being conveyed through the apparatus, the water from the bottom vessel being pumped up by means of pumps 17a, . . . , 17b, . . . 17n. The zones are closed by covers 18a, 18b, . . . , 18n.

The zone 14a, which is located closest to the heat unit, illustrates a heating area which is adapted for initial heating of the products and is supplied with water as required from the first pipeline 12 by opening a second open/closed valve 21 (on/off valve) of a pipe 22, which leads from the first pipeline 12 and down to the bottom vessel 15a.

At each of the zones, for example 14b, where supply of hot or cold water is required, the first pipeline 12 and the second pipeline 13 are interconnected by a three-way valve 19b. The third duct of the three-way valve 19b is connected to the pipeline 16b via an analog valve 20b.

Hot water can either be carried from the first pipeline 12 or cold water from the second pipeline 13 to the analog valve 20b by means of the three-way valve 19b.

As long as the temperature of the sprinkling water in the zone 14b is within the predetermined temperature, which may for example be predetermined to be approximately 65° C., the three-way valve 19b and the analog valve 20b are kept shut so that water is not supplied to the pipeline 16b.

In these circumstances there will be a constant amount of water in circulation in the zone 14b.

However, if the temperature of the sprinkling water differs from the predetermined temperature in the zone 14b, a given amount of hot or cold water can be supplied from the analog valve 20b into the pipeline 16b, in dependence of the adjustment of the three-way valve 19b and the analog valve 20b, whereby the temperature of the sprinkling water in the zone 14b can be increased or reduced as needed.

The amount of water in the zone 14b will thus increase, and the excess amount of water is carried away via an overflow of the bottom vessel 15b and return from there via a return pipe 24 to the storage tank 5 in the heat unit. The products continue progressing through the apparatus and into the cooling area, which is not illustrated in the drawing, where the products are cooled down. If the products are not cooled down, the number of Pasteurization Units (PU), a measure of the degree of pasteurization, will continue to increase.

In the cooling area the zone or the zones will be supplied with cold water as needed from the second pipeline 13 by opening of an open/closed valve (on/off valve) of a pipe, which leads from the second pipeline 13 down into the bottom vessel in a similar manner as that described for the arrangement in zone 14a.

In the event the conveyor belt 2a, 2b must be stopped due to a failure of equipment further ahead in the bottling unit, the products which are in the warmer zones of the heat area, will achieve a higher degree of pasteurization than the predetermined degree during the stationary operation of the known apparatus, which will occur already before it enters the pasteurization area. When the apparatus is again started later, these products will therefore become overpasteurized.

Products which are in the pasteurization area during a failure of equipment will be exposed to the warm sprinkling water during the entire duration of the interruption and therefore achieve a degree of pasteurization, which by far exceeds the prescribed degree.

This problem is eliminated according to the invention by opening the three-way valve 19b for admission of cold water from the second pipeline 13 to the analog valve 20b, which on its part is opened to lead cold water to the pipeline 16b to the effect that the sprinkling water in the zone 14b becomes substantially colder than before, and the temperature of the products is reduced, whereby the increase of the degree of pasteurization is slowed down.

This solution of the problem, however, involves the risk of underpasteurization of the products, when the apparatus is again started up following an interruption of operation in order to reach the constant speed for the conveyor belts 2a, 2b.

In order to achieve a sufficient pasteurization, which is measured in PU, of the products which are underpasteurized as a result of the interruption, it is necessary within a very short time to supply an extra large amount of hot water to the zone in question, and this is for example for the zone 14b achieved by opening the three-way valve 19b to carry hot water from the first pipeline 12 to the analog valve 20b, which is opened in order to carry the maximum amount of hot water possible further on to the pipeline 16.

At the same time the on/off valve 11 is shut off to the effect that the maximum amount of hot water possible is carried from the second pipe 10 and out into the first pipeline 12.

The storage tank 5 with its large content of hot water, which preferably is kept at a temperature between 85° and 90° C. by means of the heat exchanger 7, ensures a sufficient large heat capacity for fast heating of the products, until then underpasteurized, to the effect that the products have achieved the prescribed number of PU after their passage through the apparatus 1.

When water is returned to the storage tank 5 via overflows in the individual bottom vessels 15a, 15b, . . . , 15n, any fragments of broken glass from containers, which have broken during heating and cooling will remain in their respective bottom vessels to the effect that they are not carried to the heat exchanger 7 in the heat unit and thus risk clogging up of the unit.

Furthermore, a substantial amount of encrustation in the heat exchanger 7 is withheld in the storage tank 5 to the effect that this amount will not subsequently be sprayed out into the zones together with the sprinkling water.

The heat exchanger 7 may advantageously be opened at both ends by means of removable end covers 23, and because it is provided with interior rectilinear pipes, cleaning and maintenance are facilitated.

Since the water in the storage tank 5 is circulating constantly at a temperature between 85° and 90° C., micro-organisms and slime from the water in the storage tank 5 are eliminated, as a result of which the hot water which is carried to the zones in order to heat the sprinkling water will not contain micro-organisms.

A tunnel pasteurizer normally requires supply of energy, even in normal operation. With the method and the apparatus according to the invention this requirement is reduced to a minimum consumption of hot water which must be added to the sprinkling water in order to ensure that its temperature is maintained at the predetermined temperature in the zones. Since the hot water, which is added to the sprinkling water, does not contain micro-organisms, and since all the water has passed the storage tank 5 after a certain time, the need for additives is reduced.

In contrast to the known pasteurizers, which are provided with several heat exchangers, the apparatus according to the invention has one heat exchanger only, and as a result the return pipe system for condensate is also simpler as compared to the known apparatuses because in this case there is only a single connection point for condensate.

I claim:

1. In a method for the pasteurization of a continuous line of products in an apparatus having a heating area, a pasteurization area and a cooling area as well as conveyance means for carrying the products through the areas in the order indicated in a regular motion from an inlet of the apparatus to an outlet thereof, so that heating, pasteurization and cooling are effected by heat transfer between the products and a fluid, preferably water, which is sprinkled over the products, the areas being divided into zones extending in the direction of motion of the products, and the temperature of the fluid in the individual zone being controlled to the desired sequence of the heat transfer for the zone, with one of said zones having sprinkling fluid at a highest temperature, the improvement comprising:
    a) a heating fluid in a heat unit comprising a heat insulated storage tank and a single source of heat;
    b) constantly circulating the heated fluid through the heat unit;
    c) maintaining the heated fluid in the heat unit at a temperature substantially higher than the temperature of the sprinkling fluid in the zone having the highest temperature;
    d) taking the heated fluid out under low pressure from the heat unit; and
    e) supplying the heated fluid taken out under low pressure in a controlled amount directly from the heat unit to each zone in which the products are to be heated.

2. The method of claim 1, further comprising the step of maintaining the heated fluid in the heat unit at a temperature between 85° and 90° C.

3. The method of claim 1 or 2, wherein the source of heat is a fluid/steam heat exchanger and further comprising the step of controlling the steam in the heat exchanger with an analog steam valve.

4. In an apparatus for the pasteurization of a continuous line of products having a heating area, a pasteurization area and a cooling area as well as conveyance means (2a, 2b, 3a, 3b) for carrying the products through the areas in the order indicated in a regular motion from an inlet of the apparatus (1) to an outlet thereof, so that heating, pasteurization and cooling are effected by heat transfer between the products and a fluid, preferably water, which is sprinkled over the products, the areas being divided into zones (14a, 14b, . . . , 14n) extending in the direction of motion of the products, and the temperature of the fluid in the individual zone being adapted to the desired sequence of the heat transfer for the zone, with one of said zones having sprinkling fluid at a highest temperature, the improvement comprising:
    a) a heat unit including a heat insulated storage tank (5) and a single source of heat (7) connected to the storage tank (5) for heating the fluid;
    b) circulating means for constantly circulating the fluid through the source of heat and the storage tank (5);
    c) a first pipeline (12) extending from the heat unit for supplying heated fluid directly to each zone;
    d) a second pipeline (13) for cold fluid supply;
    e) a three way valve (19b . . . ) interconnecting said pipelines (12, 13) at each zone (14b, . . . ) to be heated;
    f) an analog valve (20b . . . ) connected between a third duct of said three-way valve and a third pipeline (16b, . . . ) for admission of sprinkling fluid selectively from said first and second pipelines (12, 13) to the zone (14b, . . . ); and
    g) control means for maintaining the fluid in said heat unit at a temperature, which substantially exceeds the temperature of the sprinkling water in the zone (14b) having the highest temperature.

5. The apparatus of claim 4, wherein the zone (14a), which is located nearest to the heat unit, is a heating zone, and a bottom vessel (15a) of the zone (14a) is connected to the first pipeline (12) via an analog valve (21) and a pipe (22).

6. The apparatus of claim 4 or 5, wherein the heat unit includes said control means to maintain the fluid at a temperature between 85° and 90° C.

7. The apparatus of claim 4 or 5, wherein the heat unit is a fluid/steam heat exchanger (7), which is connected to a source of steam via an analog steam valve.

8. The apparatus of claim 4 or 5, wherein the source of heat (7) is a heat exchanger provided with removable end covers (23) and interior rectilinear pipes extending in the longitudinal direction of the heat exchanger.

* * * * *